（12）United States Patent
Kuu et al.

(10) Patent No.: US 8,544,183 B2
(45) Date of Patent: Oct. 1, 2013

(54) THERMAL SHIELDING TO OPTIMIZE LYOPHILIZATION PROCESS FOR PRE-FILLED SYRINGES OR VIALS

(71) Applicants: Baxter International Inc., Deerfield, IL (US); Baxter Healthcare SA, Glattpark (CH)

(72) Inventors: Wei Y. Kuu, Libertyville, IL (US); Gregory A. Sacha, Bargersville, IN (US)

(73) Assignees: Baxter International Inc., Deerfield, IL (US); Baxter Healthcare SA, Glattpark (Opifkon) (CH)

( * ) Notice: Subject to any disclaimer, the term of this patent is extended or adjusted under 35 U.S.C. 154(b) by 0 days.

(21) Appl. No.: 13/762,888

(22) Filed: Feb. 8, 2013

(65) Prior Publication Data
US 2013/0145639 A1    Jun. 13, 2013

Related U.S. Application Data

(63) Continuation of application No. 12/649,642, filed on Dec. 30, 2009, now Pat. No. 8,371,039.

(51) Int. Cl.
*F26B 5/06*    (2006.01)

(52) U.S. Cl.
USPC ................. 34/92; 165/185; 62/114; 206/438

(58) Field of Classification Search
USPC .................... 34/284, 389, 92; 165/185, 195; 62/114, 115, 116; 206/438
See application file for complete search history.

(56) References Cited

U.S. PATENT DOCUMENTS

| 3,118,742 A | 1/1964 | McNair et al. |
| 3,128,158 A | 4/1964 | Colvin et al. |

(Continued)

FOREIGN PATENT DOCUMENTS

| EP | 0317411 A1 | 5/1989 |
| EP | 1166742 A2 | 1/2002 |
| EP | 1267139 A1 | 12/2002 |

OTHER PUBLICATIONS

Kuu et al., Determination of shelf heat transfer coefficients along the shelf flow path of a freeze dryer using the shelf fluid temperature perturbation approach, *Pharm. Dev. Technol.*, 12:485-94 (2007).

(Continued)

*Primary Examiner* — Steve M Gravini
(74) *Attorney, Agent, or Firm* — Marshall, Gerstein & Borun LLP (57) ABSTRACT

A device for supporting at least one vessel containing a target material to be lyophilized generally includes a support panel, a central region, a perimeter region, a thermal shield, and at least one shielding cavity. The support panel has a support surface. The central region is defined by the support panel for supporting the at least one vessel. The perimeter region is also defined by the support panel and surrounding the central region. The thermal shield is positioned about the perimeter region and extends transverse to the support surface of the support panel such that the thermal shield and the support panel define a storage space for accommodating the at least one vessel. The at least one shielding cavity is defined by the thermal shield and contains a shielding material during a lyophilization process. The shielding material is distinct from the target material.

19 Claims, 11 Drawing Sheets

(56) References Cited

U.S. PATENT DOCUMENTS

| | | | |
|---|---|---|---|
| 3,192,645 A | 7/1965 | Oetjen et al. | |
| 3,199,217 A | 8/1965 | Oldenkamp et al. | |
| 3,241,250 A | 3/1966 | Broadwin | |
| 3,243,892 A | 4/1966 | Ullrich et al. | |
| 3,245,152 A | 4/1966 | Natelson et al. | |
| 3,280,470 A | 10/1966 | Kuntz | |
| 3,289,314 A | 12/1966 | Porta | |
| 3,290,788 A * | 12/1966 | Seelandt | 34/294 |
| RE28,965 E | 9/1976 | Hamilton | |
| 4,017,983 A | 4/1977 | Fraser | |
| 4,060,911 A | 12/1977 | Weiler et al. | |
| 4,081,914 A | 4/1978 | Rautenbach et al. | |
| 4,090,312 A | 5/1978 | Fraser | |
| 4,177,544 A | 12/1979 | Bischkopf et al. | |
| 4,254,768 A | 3/1981 | Ty | |
| 4,953,299 A | 9/1990 | Gimeno et al. | |
| 5,020,237 A * | 6/1991 | Gross et al. | 34/265 |
| 5,035,065 A | 7/1991 | Parkinson | |
| 5,320,603 A | 6/1994 | Vetter et al. | |
| 5,489,266 A | 2/1996 | Grimard | |
| 5,680,713 A | 10/1997 | Forbert et al. | |
| 5,884,413 A | 3/1999 | Anger | |
| 6,199,297 B1 | 3/2001 | Wisniewski | |
| 6,440,101 B1 | 8/2002 | Grabenkort et al. | |
| 6,564,471 B1 | 5/2003 | Sutherland et al. | |
| 6,722,054 B2 | 4/2004 | Yarborough et al. | |
| 6,745,490 B2 | 6/2004 | Akimoto et al. | |
| 6,920,701 B2 | 7/2005 | Haseley et al. | |
| 7,334,346 B2 | 2/2008 | Nomine | |
| 8,371,039 B2 * | 2/2013 | Kuu et al. | 34/284 |
| 2001/0056272 A1 | 12/2001 | Yagi et al. | |
| 2008/0028632 A1 | 2/2008 | Py | |
| 2008/0276482 A1 | 11/2008 | Broughall et al. | |
| 2009/0205363 A1 * | 8/2009 | De Strulle | 62/533 |
| 2011/0154681 A1 | 6/2011 | Kuu et al. | |
| 2011/0155620 A1 | 6/2011 | Kuu | |
| 2012/0077971 A1 | 3/2012 | Kuu | |

OTHER PUBLICATIONS

Kuu et al., Rapid determination of dry layer mass transfer resistance for various pharmaceutical formulations during primary drying using product temperature profiles, Int. J. Pharm., 313:99-113 (2006).

Kuu et al., Rapid determination of vial heat transfer parameters using tunable diode laser absorption spectroscopy (TDLAS) in response to step-changes in pressure set-point during freeze-drying, *J. Pharm. Sci.*, 98:1136-54 (2009).

Extended European Search Report from European application No. EP10252237.2, dated Apr. 11, 2012.

* cited by examiner

FIG. 1

(FRONT OF CHAMBER)

(FRONT OF CHAMBER)

THERMAL SHIELDING TO OPTIMIZE LYOPHILIZATION PROCESS FOR PRE-FILLED SYRINGES OR VIALS

CROSS-REFERENCE TO RELATED APPLICATIONS

This is a continuation of U.S. patent application Ser. No. 12/649,42, filed Dec. 30, 2009, and the entire contents thereof are incorporated herein by reference.

FIELD OF THE DISCLOSURE

The present disclosure is generally directed to devices, systems, and methods for conducting a lyophilization process on a target material and, more particularly, to devices, systems, and methods for obtaining a uniform temperature distribution of the target material while undergoing the lyophilization process.

BACKGROUND

Lyophilization, which can also be referred to as freeze-drying, is a dehydration process typically used to preserve a perishable target material or make the target material more convenient for transport. Lyophilization works by freezing the target material and then reducing the surrounding pressure and adding sufficient heat to allow the frozen water in the target material to sublimate directly from a solid to a gas. The gas is then removed from the target material to complete dehydration.

Conventional lyophilization processes are carried out with freeze-drying machines. A typical freeze-drying machine includes a lyophilization chamber, within which the target material is disposed during the lyophilization process. The lyophilization chamber generally includes a box-shaped structure having one or more sidewalls, a top wall, and a bottom wall. Moreover, the chamber can include one or more shelves or racks, for example, for storing the target material.

SUMMARY

One aspect of the present disclosure provides a device for supporting at least one vessel containing a target material to be lyophilized. The device includes a support panel, a central region, a perimeter region, a thermal shield, and at least one shielding cavity. The support panel has a support surface. The central region is defined by the support panel for supporting the at least one vessel. The perimeter region is also defined by the support panel and surrounding the central region. The thermal shield is positioned about the perimeter region and extends transverse to the support surface of the support panel such that the thermal shield and the support panel define a storage space for accommodating the at least one vessel. The at least one shielding cavity is defined by the thermal shield and contains a shielding material during a lyophilization process. The shielding material is distinct from the target material.

The thermal shield can optionally include an inner wall portion and an outer wall portion. The inner wall portion surrounds the central region. The outer wall portion surrounds the inner wall portion and is spaced from the inner wall portion to define the at least one shielding cavity.

The at least one shielding cavity defined between the inner and outer wall portions of the thermal shield can optionally include an elongated channel surrounding the central region of the support panel and for containing the shielding material.

The device can further optionally include an elongated opening defined by the elongated channel for enabling at least one component of the shielding material to exhaust from the elongated channel during the lyophilization process.

The device can further optionally include a cap enclosing the elongated channel. The cap can define a plurality of apertures for controlling a rate at which the shielding material exhausts from the channel during the lyophilization process.

The thermal shield can optionally include a plurality of shielding repositories arranged side-by-side about the perimeter region of the support panel and surrounding the central region. Each of the plurality of repositories can define a shielding cavity containing the shielding material during the lyophilization process.

Each of the shielding repositories can optionally comprise a syringe tube.

Another aspect of the present disclosure includes a system for lyophilizing target material stored within at least one vessel. The system generally includes a freeze-drying machine and the device as described herein, such as one according to any of the foregoing aspects. The freeze-drying machine includes a chamber having chamber walls, and the device is removably supported within the chamber. So configured, the thermal shield of the device substantially inhibits transmission of or absorbs thermal radiation emitted by the chamber walls of the freeze drying machine while the target material is being lyophilized, thereby facilitating a uniform temperature distribution amongst the target material stored in the at least one vessel.

A further aspect of the present disclosure includes a method of lyophilizing a target material stored in at least one vessel. The method generally includes at least partially filling at least one shielding cavity with a shielding material that includes at least one component that is different than at least one component of the target material. The at least one shielding cavity can be arranged to surround the at least one vessel. The method further includes loading the at least one vessel and the at least one shielding cavity into a lyophilization chamber of a freeze drying machine. The lyophilization chamber can have sidewalls and can be arranged and configured to support the at least one vessel and the at least one shielding cavity. The method further includes lyophilizing the target material stored in the at least one vessel. The method still further includes inhibiting transmission of or absorbing thermal radiation emitted from the sidewalls of the lyophilization chamber to prevent it from reaching the at least one vessel, thereby minimizing variations in temperature amongst the target material stored in the at least one vessel.

The method can further optionally include loading the at least one vessel onto a central region of a support panel.

The method can further optionally include with a shielding material at least partially filling at least one elongated channel that is adapted to surround the at least one vessel.

The method can further optionally include at least partially filling a plurality of repositories arranged side-by-side and adapted to surround the at least one vessel with a shielding material.

Inhibiting the thermal radiation can optionally include cooling a perimeter region within the lyophilization chamber, the perimeter region surrounding the at least one vessel and being disposed between the at least one vessel and the sidewalls of the lyophilization chamber adjacent to the shielding material.

Cooling the perimeter region can optionally include lyophilizing at least a portion of the shielding material stored in the at least one shielding cavity generally simultaneously with lyophilizing the target material stored in the at least one vessel.

DETAILED DESCRIPTION

Figure 1:
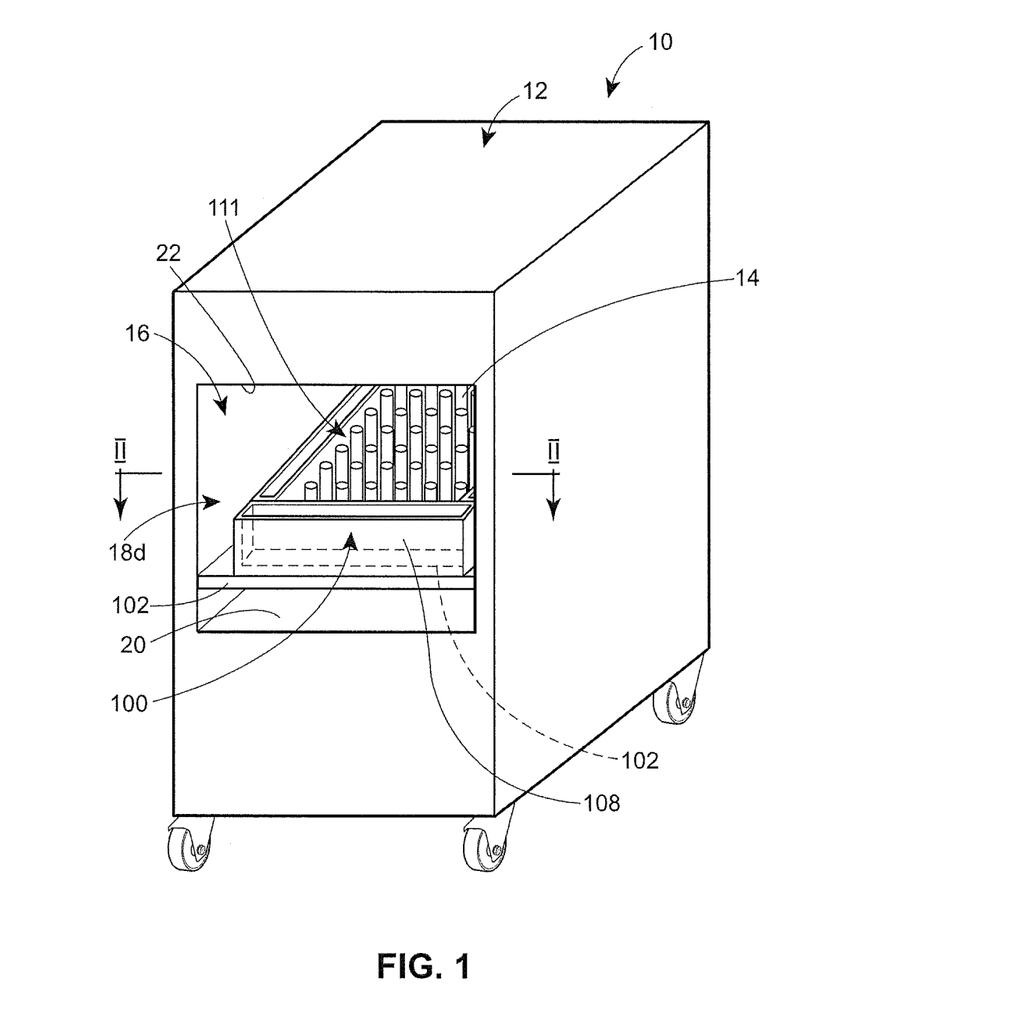
FIG. 1 is a perspective view of a system for lyophilizing a target material constructed in accordance with the principles of the present disclosure and including a freeze-drying machine accommodating a device supporting at least one vessel containing the target material.
Figure 2:
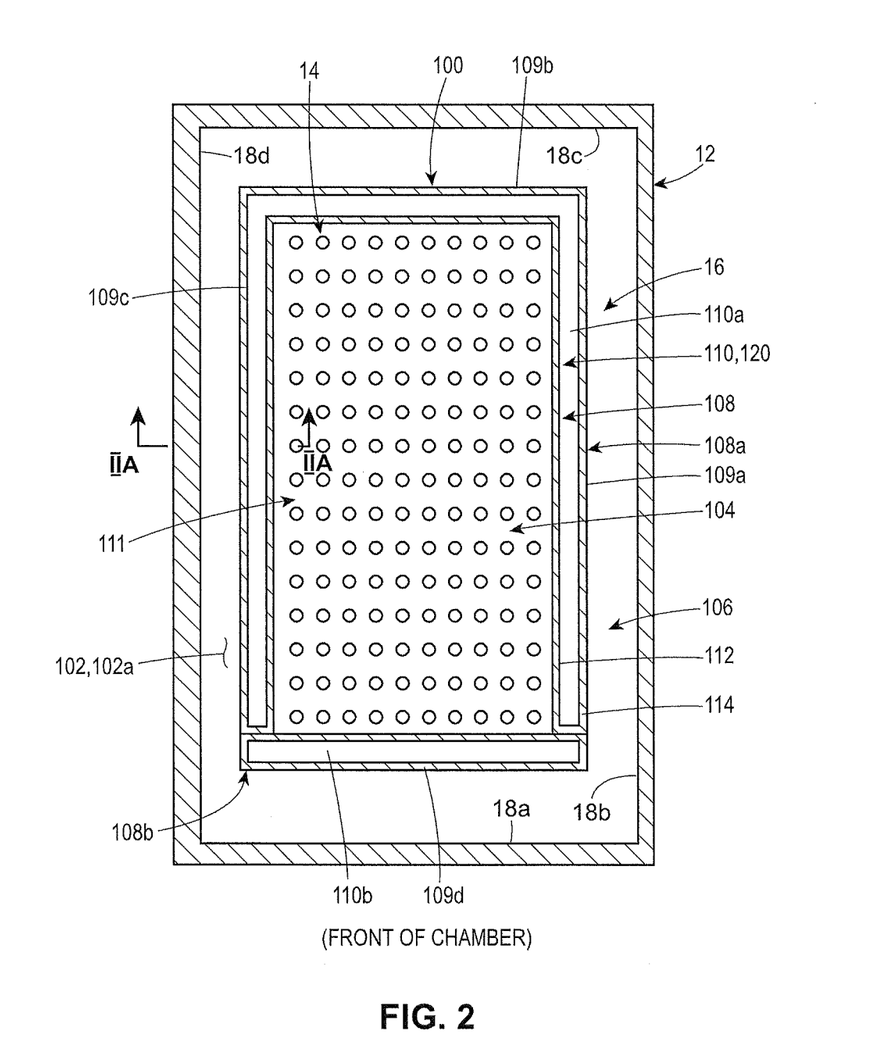
FIG. 2 is a cross-sectional view taken through line II-II of FIG. 1 and including one embodiment of a device for supporting at least one vessel of target material in accordance with the principles of the present disclosure.
Figure 2A:
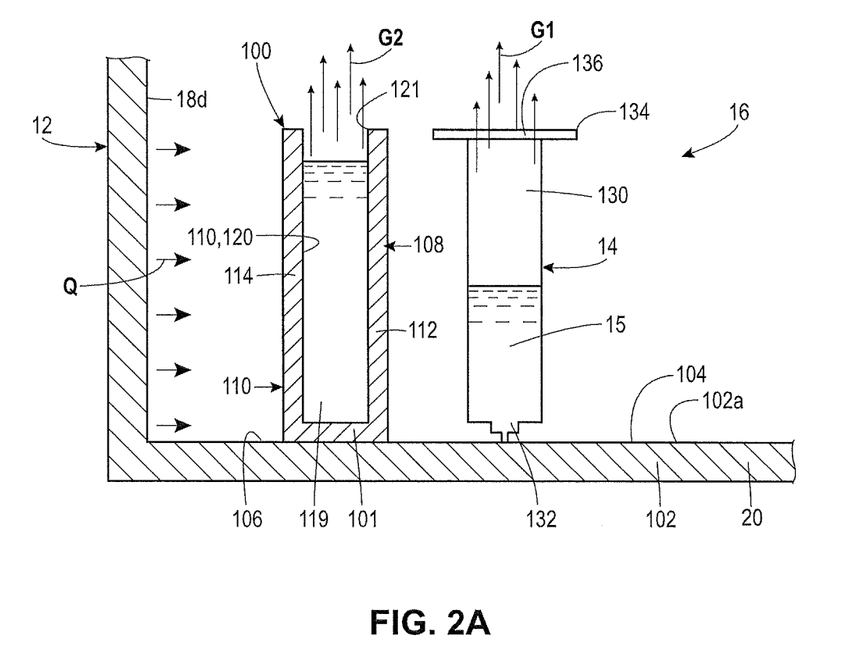
FIG. 2A is a partial cross-sectional side view taken through line IIA-IIA of FIG. 2.

FIG. 1 depicts a system 10 for lyophilizing a target material including a freeze-drying machine 12 accommodating a device 100 supporting a plurality of vessels 14 that contain the target material 15 (shown in FIG. 2A). In the present embodiment, the plurality of vessels 14 can include syringe tubes, vials, beakers, or any other material-containing device. In other embodiments, the device 100 can be arranged and configured to contain a single vessel 14 as opposed to a plurality of vessels 14. In yet another alternative embodiment, the device 100 can be arranged to directly contain the target material 15 without the need for any intervening vessel(s). The freeze-drying machine 12 defines a lyophilization chamber 16 that is selectively openable/closeable with a door (not shown), for example. The device 100 is disposed within the lyophilization chamber 16 such that the target material 15 carried within the vessels 14 can be lyophilized upon activation of the freeze-drying machine 12.

To lyophilize the target material 15, the freeze-drying machine 12 first performs a cooling step and reduces the temperature within the lyophilization chamber 16 to a temperature below the freezing point of at least one component of the target material 15, for example in the range of approximately negative twenty degrees Celsius (−20° C.) to approximately negative seventy degrees Celsius (−70° C.). Then, the freeze-drying machine 12 performs a drying step, whereby the ambient pressure of the lyophilization chamber 16 is reduced with a vacuum pump (not shown), for example, to a pressure that is substantially less than atmospheric pressure, such as a pressure in the range of approximately 1.33 Pa (0.01 Torr) to approximately 133 Pa (1 Torr). With the ambient pressure reduced, a sufficient amount of heat can be added to the lyophilization chamber 16 to sublimate the frozen water in the target material 15 from a solid to a gas. The gaseous water is then removed from the target material 15 and collected on a condenser plate (not shown), for example, such that the target material 15 remains "freeze-dried." The pressure within the lyophilization chamber 16 can then be increased or returned to the ambient pressure outside of the lyophilization chamber 16, and the vessels 14 can be removed from the freeze-drying machine 12 for packaging or further processing of the target material 15.

FIGS. 2 and 2A depict one embodiment of a device 100 for supporting the plurality of vessels 14 disposed within the lyophilization chamber 16 of the freeze-drying machine 12 of FIG. 1. As illustrated in FIG. 2, the lyophilization chamber 16 is defined between front and rear walls 18a, 18c and opposing left and right side walls 18d, 18b. The front wall 18a may be embodied by a door or other movable panel, for example, and defines the front of the freeze-drying machine 12, through which the various items are loaded into the lyophilization chamber 16. Moreover, as shown in FIG. 1, the lyophilization chamber 16 includes a bottom wall 20 located beneath the device 100 and a top wall 22 located above the device 100.

With continued reference to FIGS. 1, 2, and 2A, the device 100 includes a support panel 102, which can constitute a shelf or tray supported within the lyophilization chamber 16, and a thermal shield 108. The support panel 102 is a generally flat rectangular member having a central region 104 and a perimeter region 106. The top surface of the support panel 102 defines a support surface 102a. The perimeter region 106 of the support panel 102 surrounds, e.g., circumscribes, the central region 104. The central region 104 supports the plurality of vessels 14 and, in some embodiments, can include a plurality of recesses or other features for maintaining the position and/or alignment of the vessels 14.

The thermal shield 108 is positioned on the perimeter region 106 of the support panel 102 and defines at least one shielding cavity 110. As illustrated in FIG. 2A, the thermal shield 108 includes a bottom wall portion 101, an inner wall portion 112, and an outer wall portion 114. The bottom wall portion 101 is supported directly on the support surface 102a of the support panel 102 and the inner and outer wall portions 112, 114 extend generally parallel to each other and transverse to the bottom wall portion 101 and the support surface 102a of the support panel 102. In the present embodiment, the inner and outer wall portions 112, 114 extend perpendicularly from the bottom wall portion 101 of the thermal shield 108 and the support surface 102a of the support panel 102, as is illustrated in FIGS. 1 and 2A. The inner wall portion 112 surrounds, e.g., circumscribes, the central region 104 of the support panel 102. So configured, the thermal shield 108 and the support panel 102 define a three-dimensional storage space 111 (shown in FIG. 1) accommodating the plurality of vessels 14 of the target material 15. The outer wall portion 114 surrounds, e.g., circumscribes, the inner wall portion 112 and is spaced from the inner wall portion 112 to define the at least one shielding cavity 110. The at least one shielding cavity 110 is adapted to contain a shielding material 119 (shown in FIG. 2A) that is distinct from the target material 15.

In the embodiment of the device 100 depicted in FIG. 2, the thermal shield 108 is constructed of two separable portions including a rear portion 108a and a front portion 108b. The rear portion 108a includes a unitary or one-piece structure having first through third legs 109a-109c arranged in a U-shape such that the first leg 109a is disposed nearest the right side wall 18b of the lyophilization chamber 16, the second leg 109b is disposed nearest the rear wall 18c of the lyophilization chamber 16, and the third leg 109c is disposed nearest the front wall 18a of the lyophilization chamber 16. Furthermore, as illustrated, the front portion 108b of the present embodiment of the thermal shield 108 includes a unitary or one-piece structure including a single leg 109d positioned adjacent the open end of the U-shaped rear portion 108a of the thermal shield 108 such that the thermal shield 108 as a whole completely surrounds, i.e., circumscribes, the central region 104 of the support panel 102. As mentioned, the rear and front portions 108a, 108b of the thermal shield 108 are separable. So configured, the rear and front portions 108a, 108b can facilitate loading the thermal shield 108 and the plurality of vessels 14 into the lyophilization chamber 16. For example, to prepare the lyophilization process, the support panel 102 can first be loaded into the lyophilization chamber 16 through an opening (shown in FIG. 1) in the front of the freeze-drying machine 12. Then, the rear portion 108a of the thermal shield 108 including the first though third legs 109a-109c can be loaded onto the support panel 102 through the opening in the front of the freeze-drying machine 12. Then, the plurality of vessels 14 containing target material 15 can be loaded onto the central region 104 of the support panel 102 through the opening in the front of the freeze-drying machine 12. Finally, the front portion 108b of the thermal shield 108 can be loaded into the lyophilization chamber 16 and on the support panel 102 adjacent the rear portion 108a, as depicted in FIG. 2.

Figure 10:
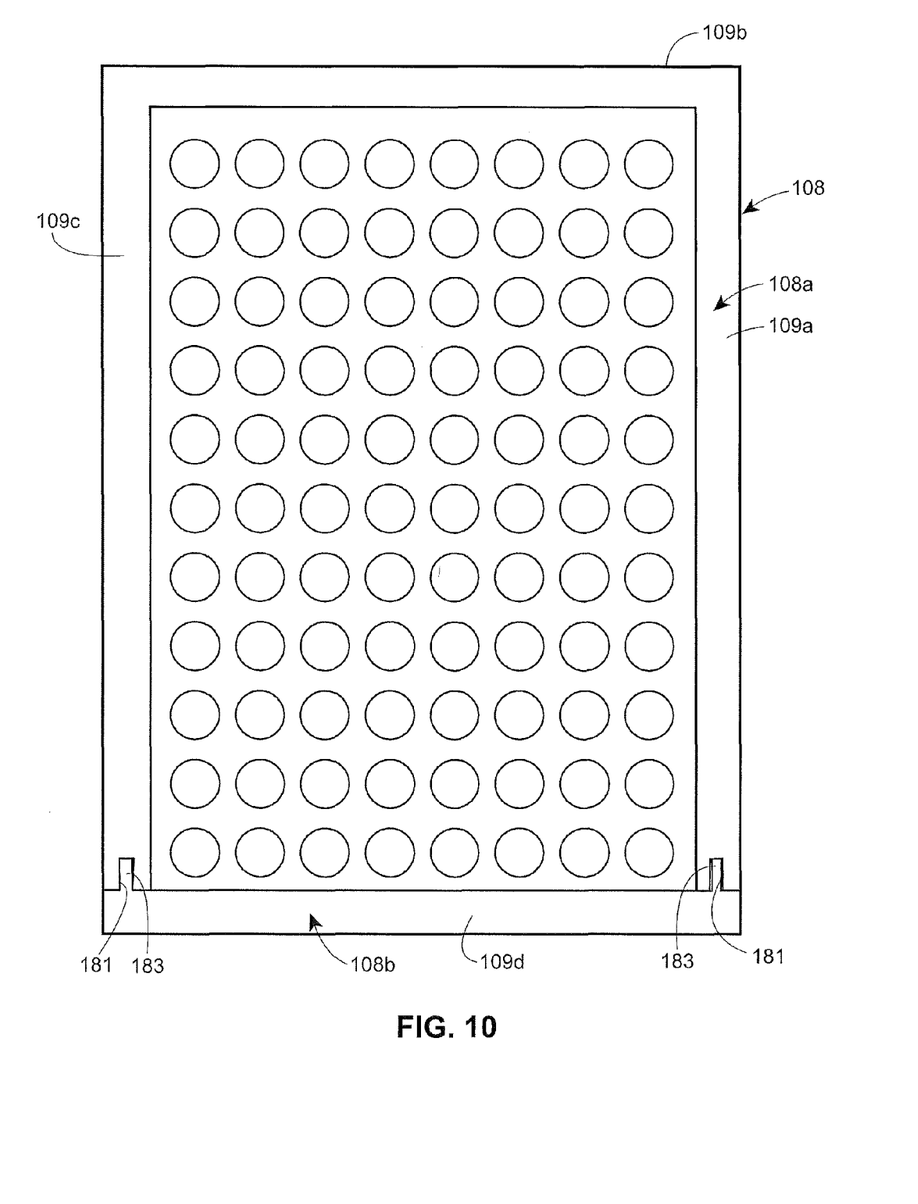
FIG. 10 is a plan view of a device supporting a plurality of vessels containing a target material and illustrating a thermal shield including two interlocked pieces.

In the embodiment illustrated in FIG. 2, the front portion 108b of the thermal shield 108 abuts up against ends of the first and third legs 109a, 109c of the rear portion 108a of the thermal shield 108. In an alternative embodiment, which is illustrated in FIG. 10, the rear and front portions 108a, 108b of the thermal shield 108 can interlock. For example, as illustrated in FIG. 10, the ends of the first and third legs 109a, 109c of the rear portion 108a of the thermal shield 108 can include recesses 181 and the leg 109d of the front portion 108b can include tongues 183 that are adapted to be removably disposed within the recesses 181. This interlocking connection can assist in aligning the rear and front portions 108a, 108b of the thermal shield 108.

Referring back to FIG. 2, with the thermal shield 108 configured to include the rear and front portions 108a, 108b, as described, the shielding cavity 110 is divided into two shielding cavity portions including U-shaped a rear shielding cavity portion 110a defined by the rear portion 108a of the thermal shield 108 and a straight front shielding cavity portion 110b defined by the front portion 108b of the thermal shield 1108. Each shielding cavity portion 110a, 110b, and therefore, the shielding cavity 110 as a whole can be described as including an elongated channel 120 defining an elongated opening 121 (shown in FIG. 2A) at a location opposite the inner and outer wall portions 112, 114 from the bottom wall portion 101. The elongated opening 121 opens the elongated channel 120 to the ambient atmosphere of the lyophilization chamber 16 when the device 100 is disposed in the freeze-drying machine 12.

The elongated channel 120 surrounds, e.g., circumscribes, both the inner wall portion 112 of the thermal shield 108 and the central region 104 of the support panel 102. As such, the elongated channel 120 also surrounds, e.g., circumscribes, the plurality of vessels 14 supported on the support panel 102.

In the embodiment depicted in FIG. 2A, each of the vessels 14 includes a conventional syringe tube 130 having a reduced-diameter tip portion 132 and a base portion 134. The tip portion 132 of each syringe tube 130 can include a sealed orifice (not shown), for example, that is adapted to receive a hypodermic need for delivering a liquid material out of the syringe tube 130. In the disclosed embodiment, the tip portion 132 of each syringe tube 130 is supported on the support surface 120a within the central region 104 of the support panel 120. The base portion 134 of the syringe tube 130 defines a circular opening 136 that is adapted to receive a syringe plunger (not shown) in a conventional manner. As shown in FIG. 2A, syringe plungers are not included within the syringe tubes 130 during the lyophilization process such that the target material 15 is in direct communication with the ambient atmosphere of the lyophilization chamber 16 via the openings 136.

With this arrangement of the device 100, the thermal shield 108 is disposed between, e.g., separates, the front, rear, and side walls 18a-18d of the lyophilization chamber 16 and the plurality of vessels 14, as depicted in FIGS. 2 and 2A. So configured, the thermal shield 108 can insulate the vessels 14 by substantially inhibiting and/or preventing thermal radiation that is emitted by the walls 18a-18d of the lyophilization chamber 16 from reaching the vessels 14 while the target material 15 is being lyophilized, e.g., by blocking transmission and/or by absorbing the energy. This shielding can help ensure that the temperature of the target material 15 across the plurality of vessels 14 is generally uniform at any given time during the lyophilization process, which provides uniformity and quality assurance of the dehydrated target material 15.

For example, as depicted in FIG. 2A, the shielding cavity 110 of the thermal shield 108, which in the present embodiment includes the elongated channel 120, is adapted to contain a shielding material 119. As such, the shielding material 119 is disposed between, e.g., separates, the walls 18a-18d of the lyophilization chamber 16 and the vessels 14 containing the target material 15. The shielding material 119 can, for example, include a liquid, wherein at least one component of the liquid is water. The shielding material 119 can optionally include only water. In other embodiments, the shielding material 119 could foreseeably include other liquids, or even gases, or solids, so long as the selected shielding material 119 serves one or more principles of the disclosure. Preferably, the shielding material has a phase change interface (e.g., sublimation curve or melting curve) within the temperature and pressure ranges employed in lyophilizatin of the target material 15. Preferably, the shielding material 119 is a liquid at room temperature which can be sublimated during lyophilizatin of the target material 15.

As discussed above, during lyophilization, the ambient temperature of the lyophilization chamber 16 can be reduced during a cooling step to a temperature in the range of approximately negative twenty degrees Celsius (−20° C.) to approximately negative seventy degrees Celsius (−70° C.), for example. In this temperature range, the shielding material 119 and the target material 15 freeze solid. Then, during a drying step, the ambient pressure in the lyophilization chamber 16 is reduced and sufficient heat can be added to sublimate the target material 15. Sublimation generally includes transitioning any solid frozen water that is in the target material 15 directly to the gaseous phase. The water in the gaseous phase is then exhausted from the target material 15 through the circular openings 136 of the vessels 14, as indicated with arrows G1 in FIG. 2A, for example.

During this lyophilization process, the arrangement and configuration of the thermal shield 108 of the present embodiment serves as a physical barrier, e.g., insulator, that substantially inhibits or prevents thermal radiation Q emitted from the walls 18a-18d from reaching the target material 15. In the absence of the thermal shield 108, the thermal radiation Q can raise the temperature of the target material 15 stored in some of the vessels 14. The target material 15 stored in the vessels 14 nearest the walls 18a-18d can experience the greatest impact from the radiation. As such, the target material 15 stored within these outer-most vessels 14 would otherwise lyophilize at a different rate than the target material 15 stored in the more interior vessels 14. Such varying rates of lyophilization can result in end product of varying quality.

In addition to providing a physical barrier, e.g., insulator, the thermal shield of the present embodiment can provide a sublimation cooling effect to combat the influence of thermal radiation on the target material 15 by absorbing such energy at steady-state temperature via phase change of the shielding material 119. For example, when the target material 15 is lyophilized, as described above, any water in the shielding material 119 stored in the thermal shield 108 of the present embodiment at least partly sublimates. That is, as the pressure in the lyophilization chamber 16 is reduced and heat is added, any water within the shielding material 119 transitions from a solid, e.g., frozen material, to a gas and the gas exhausts from the elongated channel 120 through the elongated opening 121 in the thermal shield 108, as indicated with arrows G2 in FIG. 2A.

During this phase change, the shielding material 119 will absorb thermal radiation Q emitted by the chamber side walls, which in the present embodiment includes at least the walls 18a-18d. For example, as mentioned above, lyophilizing the target material 15 can generally include a cooling step followed by a drying step. During the drying step, the ambient pressure is reduced and sufficient heat can be added such that components of both the target material 15 and the shielding material 119 transition directly from a solid to a gas. With the pressure maintained in this reduced state, any additional heat added to the shielding material 119 will increase the rate of sublimation. Accordingly, when the thermal radiation Q emitted by the walls 18a-18d of the lyophilization chamber 16 acts on the shielding material 119, the sublimation rate of the shielding material 119 increases, while the actual temperature of the shielding material 119 stays the same. As such, it can be said that the shielding material 119 absorbs any excess energy emitted by the walls 18a-18d, for example, such that all of the target material 15 stored in the vessels 14 can be maintained at a uniform temperature. The foregoing configuration can be described as providing a sublimation cooling effect that advantageously substantially inhibits or prevents thermal radiation Q emitted by the walls 18a-18d of the lyophilization chamber 16 from reaching the target material 15 stored in the vessels 14.

While the foregoing embodiment of the device 100 has been described as being configured to support a plurality of vessels 14 that constitute syringe tubes 130 arranged in a "tip-down" orientation, i.e., with their tip portions 132 engaging the support panel 102, alternative embodiments of the device 100 can include the syringe tubes 130 arranged in a "tip-up" orientation, i.e., with their base portions 134 engaging the support panel 102. In such an embodiment, the syringe tubes 130 can receive plungers to seal the circular openings 136 at the base portions 134 and the gaseous water can exit from an opening in the tip portions 132 that is adapted to receive a hypodermic needle. Moreover, as mentioned above, still further alternative embodiments could include at least some of the vessels 14 being embodied by vials, beakers, or generally any other structure capable of storing the target material 15.

Figure 3:
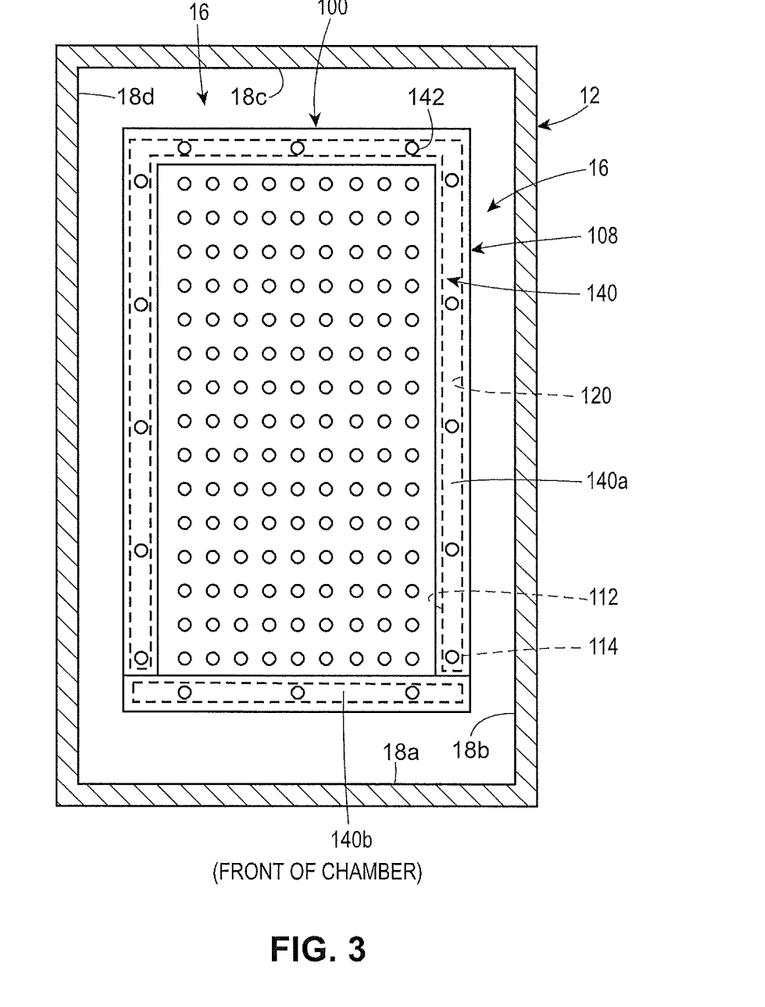
FIG. 3 is a cross-sectional view taken through line II-II of FIG. 1 and including an alternative embodiment of a device for supporting at least one vessel of target material in accordance with the principles of the present disclosure.

While the thermal shield 108 of the device 100 has thus far been disclosed as including an elongated channel 120 having an elongated opening 121 in direct communication with the lyophilization chamber 16 for exhausting the sublimated water of the shielding material 119, alternative embodiments could be constructed differently. For example, FIG. 3 depicts a modified version of the device 100 depicted in FIGS. 2 and 2A further including a cap 140 at least partly enclosing the elongated channel 120 of the thermal shield 108. The cap 140 can control the flow of the sublimated shielding material 119 as it exhausts from the channel 120 by restricting the ability of the gas to exit the channel 120. But for the inclusion of the cap 140, the modified version of the device 100 depicted in FIG. 3 is otherwise identical to the device 100 described above with reference to FIGS. 2 and 2A. As such, the thermal shield 108 includes rear and front portions 108a, 108b, and the cap 140 includes corresponding rear and front cap portions 140a, 140b.

As shown, the cap 140 includes an elongated member in the same shape as the channel 120 and defines a plurality of apertures 142, through which the sublimated shielding material 119 is able to exhaust. Only one aperture 142 is identified by reference numeral in FIG. 3 for the sake of clarity. The disclosed embodiment of the cap 140, which includes both the rear cap portion 140a and the front portion 140b, includes sixteen apertures (16) of common diameter generally equally spaced along the length of the cap 140. Alternative embodiments, however, can include generally any number of apertures, any size of apertures, or any mixture of sizes and/or spacing of apertures. The combined area of the plurality of apertures 142 of the cap 140 is substantially smaller than the overall area of the elongated opening 121 of the thermal shield 108 described above with reference to FIGS. 2 and 2A. As such, the plurality of apertures 142 can control, e.g., decrease and/or increase, a rate at which the sublimated shielding material 119 can exhaust out of the channel 120 relative to the elongated opening 121. By controlling the rate at which the sublimated shielding material 119 exhausts from the elongated channel 120, the degree to which the sublimation cooling effect cools the thermal shield 108 and perimeter region of the lyophilization chamber 16, thereby insulating the target material 15 can be controlled.

As depicted, the cap 140 of the present embodiment extends the entire length of the channel 120 and is removably disposed on top surfaces of the inner and outer wall portions 112, 114 of the thermal shield 108. The cap 140 optionally can be fixed to the inner and outer wall portions 112, 114 of the thermal shield 108 with fasteners such as screws, bolts, an adhesive, a weld bead, etc. Each cap portion 140a, 140b can be constructed of a single piece of material or can be constructed of a plurality of pieces of material. In the alternative, each cap portion 140a, 140b can be constructed integrally, e.g., as a single piece, with the rear and front portions 108a, 108b of the thermal shield 108, for example.

While the foregoing embodiments of the device 100 include rear and front cavity portions 110a, 110b that each define a single contiguous cavity, e.g., a channel, for containing shielding material 119, alternative embodiments of the cavity portions 110a, 110b can each foreseeably include a plurality of distinct cavities, either bridged by a structural material to create a unitary structure comprising multiple such cavities, or connected by passageways that enable the shielding material 119 to flow between the cavities.

Furthermore, while the foregoing embodiments of the device 100 have been described as including thermal shields 108 that are constructed of inner and outer wall portions 112, 114 defining two cavity portions 110a, 110b that collectively surround, e.g., circumscribe, the target material 15, alternative embodiments of the device can include a thermal shield including any number of separate shielding cavities.

Figure 4:
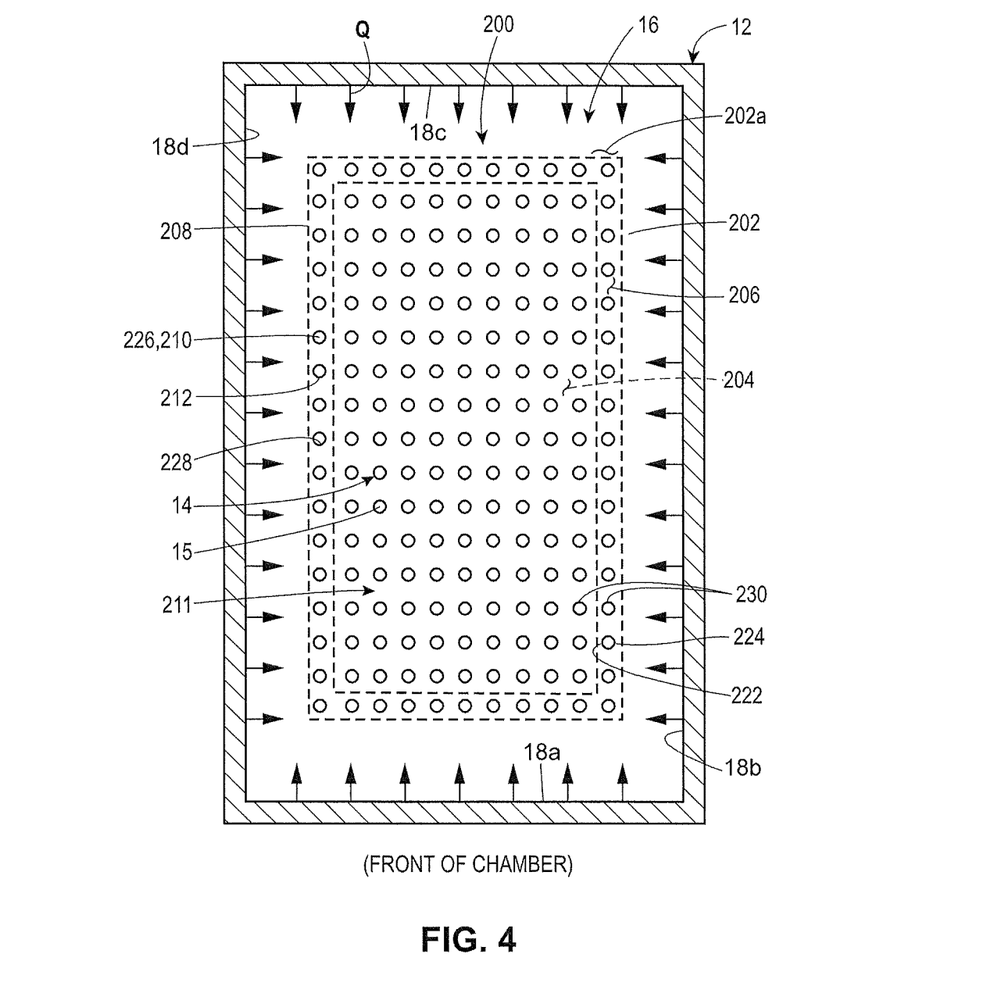
FIG. 4 is a cross-sectional view taken through line II-II of FIG. 1 and including another alternative embodiment of a device for supporting at least one vessel of target material in accordance with the principles of the present disclosure.

For example, FIG. 4 depicts one alternative embodiment of a device 200 constructed in accordance with the principles of the present disclosure and disposed within a lyophilization chamber 16 of the freeze-drying machine 12 of FIG. 1, for example. As with the device 100 described above, the device 200 includes a support panel 202 defining a support surface 202a and including a central region 204 and a perimeter region 206. These aspects are generally identical to the corresponding aspects of the device 100 described above, and therefore, the specific details will not be repeated. The central region 204 supports a plurality of vessels 14 storing target material 15 that has been lyophilized or is to be lyophilized. FIG. 4 only identifies a single vessel 14 by reference numeral for the sake of clarity.

The device 200 further includes a thermal shield 208 positioned about the perimeter region 206 of the support panel 202 and defining a plurality of shielding cavities 210, only one of which is identified by reference numeral. For the sake of description only, FIG. 4 illustrates a pair of dashed lines containing the thermal shield 208 of the device 200. The thermal shield 208 generally includes a plurality of shielding repositories 212 arranged side-by-side on the perimeter region 206 of the support panel 202. As such, the plurality of shielding repositories 212 surround, e.g., circumscribe, the central region 204 of the support panel 202 and the plurality of vessels 14 storing the target material 15.

In one embodiment, each of the plurality of repositories 212 can include a tube 230. The tubes 230 can include cylindrical tubes having circular openings 228. The tubes 230 can include shielding material 119, as described herein. For the sake of description, the cylindrical tubes can also be described as including inner and outer wall portions 222, 224 extending generally transverse to, e.g., perpendicular to, the support surface 202a of the support panel 202. So configured, it can be said that the tubes 230 of the thermal shield 20 and the support panel 202 of the present embodiment of the device 200 depicted in FIG. 4 define a three-dimensional storage space 211 accommodating the plurality of vessels 14. The inner wall portion 222 of each of the plurality of shielding repositories 212 is disposed facing the plurality of vessels 14, and the outer wall portion 224 of each of the plurality of shielding repositories 212 is disposed facing one of the walls 18a-18a of the lyophilization chamber 16.

In the embodiment of the device 200 depicted in FIG. 4, the cylindrical shielding repositories 212 define the shielding cavities 210 as including cylindrical cavities 226. Each cylindrical cavity 226 is open to the ambient atmosphere of the lyophilization chamber 16 via the circular opening 228 of the respective shielding repository 212 when the device 200 is disposed in the freeze-drying machine 12.

With the device 200 configured as described, the thermal shield 208 functions similar to the thermal shields 108 described above with reference to FIGS. 2-3 in that the plurality of shielding repositories 212 serve as physical barriers, e.g., insulators, to substantially inhibit or prevent thermal radiation Q emitted by the walls 18a-18d of the lyophilization chamber 16 from reaching the target material 15 stored in the plurality of vessels 14. Moreover, the thermal shield 208 of the present embodiment of the device 200 can also optionally provide a sublimating cooling effect as described above by selection of an appropriate shielding material 119.

While the plurality of repositories 212 of the thermal shield 208 of the embodiment of the device 200 depicted in FIG. 4 have been described as including a plurality of tubes, in alternative embodiments, the plurality of repositories 212 could include vials, beakers, or generally any other structure capable of storing shielding material and insulating the vessels 14 in accordance with the principles of the present disclosure.

With any of the foregoing devices 100, 200 described herein, a method of lyophilizing the target material 15 can generally be the same. For example, before the devices 100, 200 are loaded into the lyophilization chamber 16, the one or more shielding cavities 110, 210 can be at least partially filled with shielding material 119. Additionally, each of the vessels 14 must be at least partially filled with target material 15. With the shielding cavities 110, 210 and vessels 14 filled, the device 100, 200 can be loaded into a lyophilization chamber 16 of a freeze-drying machine 12. When the thermal shield 108, 208 of the device 100, 200 includes rear and front portions 108a, 108b, as described above with reference to FIGS. 2 and 2A, the rear portion 108a is first loaded onto the support panel 102 in the lyophilization chamber 16. Then, the vessels 14 can be loaded, and finally, the front portion 108b can be loaded. Once everything is loaded, the lyophilization process can be activated to lyophilize the target material 15 stored in the vessels 14. While the target material 15 is being lyophilized, it should be appreciated that the thermal shield 108, 208 substantially inhibits or prevents any thermal radiation emitted from the sidewalls 18a-18d of the lyophilization chamber 16 from reaching the vessels 14, as described above.

Figure 5:
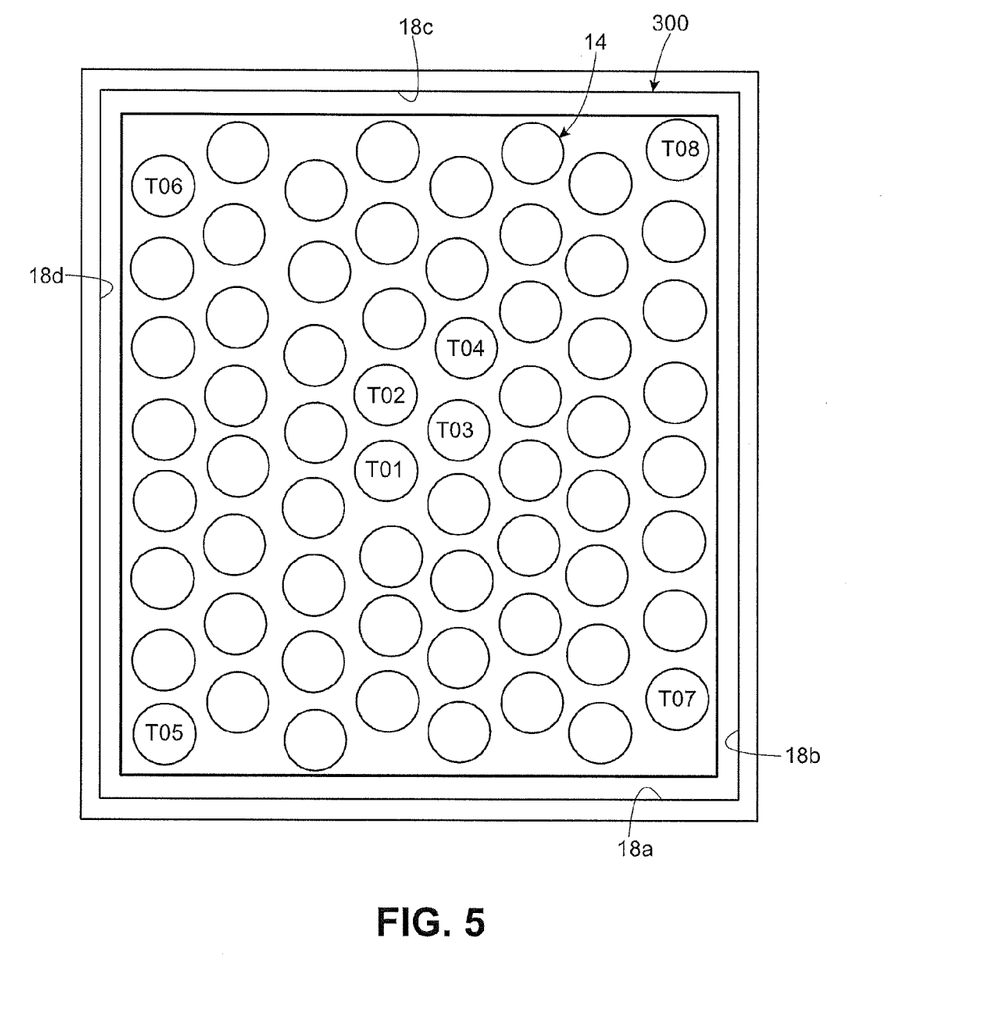
FIG. 5 is a plan view of a device supporting a plurality of vessels containing a target material and indicating the position of a plurality of temperature probes utilized during a test lyophilization process.

In some embodiments, the thermal shield 108, 208 can inhibit the thermal radiation from reaching the vessels by serving as a physical barrier, e.g., an insulator, between the vessels 14 and the walls 18a-18d of the chamber 16. In some embodiments, the thermal shield 108, 208 provides a sublimation cooling effect. FIG. 5 in combination with FIGS. 6-9 illustrate the results of testing, which has substantiated the benefits and advantages of the foregoing subject matter.

Specifically, FIG. 5 illustrates a plan view of a test apparatus 300 that was set up including a plurality of vessels 14 arranged in an array and containing target material 15 to be lyophilized in a lyophilization chamber such as the lyophilization chamber 16 of the freeze-drying machine 12 depicted in FIG. 1, for example. As such, FIG. 5 also illustrates the walls 18a-18d of the chamber 16. The apparatus 300 is equipped with a plurality of temperature probes T01-T08 disposed within a variety of vessels 14. The first through fourth probes T01-T04 are located in vessels 14 at the substantial center of the array of vessels 14. The fifth through eighth T05-T05 probes are located in vessels 14 at the corners of the array of vessels 14.

Figure 6:
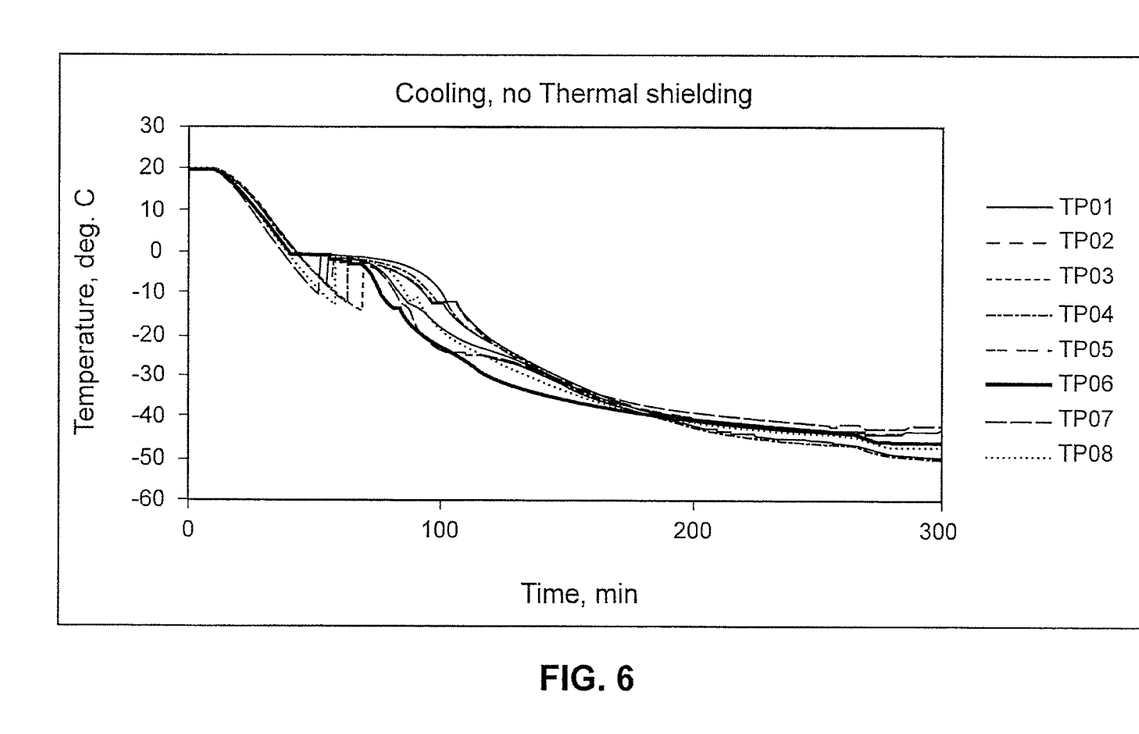
FIG. 6 is a graphical representation of the temperatures sensed by the plurality of temperature probes of FIG. 5 during a cooling step of the test lyophilization process conducted without the use of a thermal shield of the present disclosure.
Figure 8:
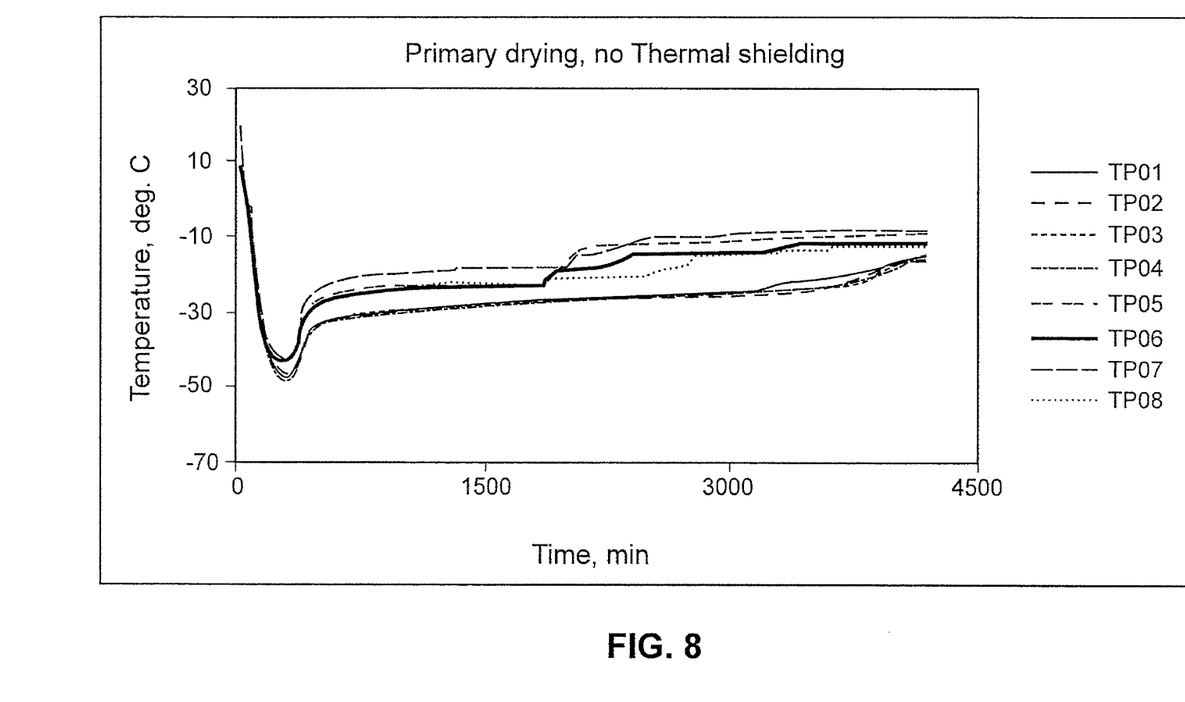
FIG. 8 is a graphical representation of the temperatures sensed by the plurality of temperature probes of FIG. 5 during a drying step of a test lyophilization process conducted without the use of a thermal shield of the present disclosure.

FIGS. 6 and 8 graphically illustrate the temperatures sensed by the temperature probes T01-T08 during the cooling step and the drying step of a test lyophilization process, respectively, wherein the apparatus 300 of FIG. 5 was not equipped with a thermal shield 108. As illustrated, the lines on the graph, each of which is assigned to a particular temperature probe T01-T08, show non-uniformity in temperature at the various locations monitored, particularly between the center and the outside of the array of vessels 14.

Figure 7:
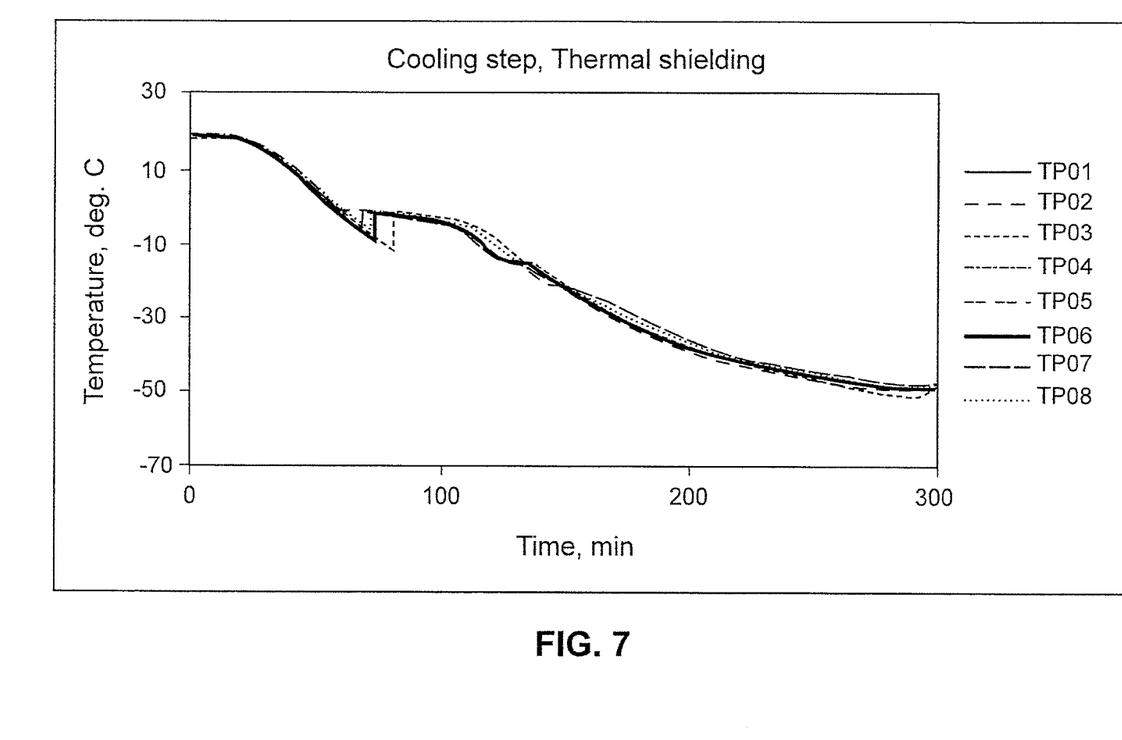
FIG. 7 is a graphical representation of the temperatures sensed by the plurality of temperature probes of FIG. 5 during a cooling step of a test lyophilization process conducted with the use of a thermal shield of the present disclosure.
Figure 9:
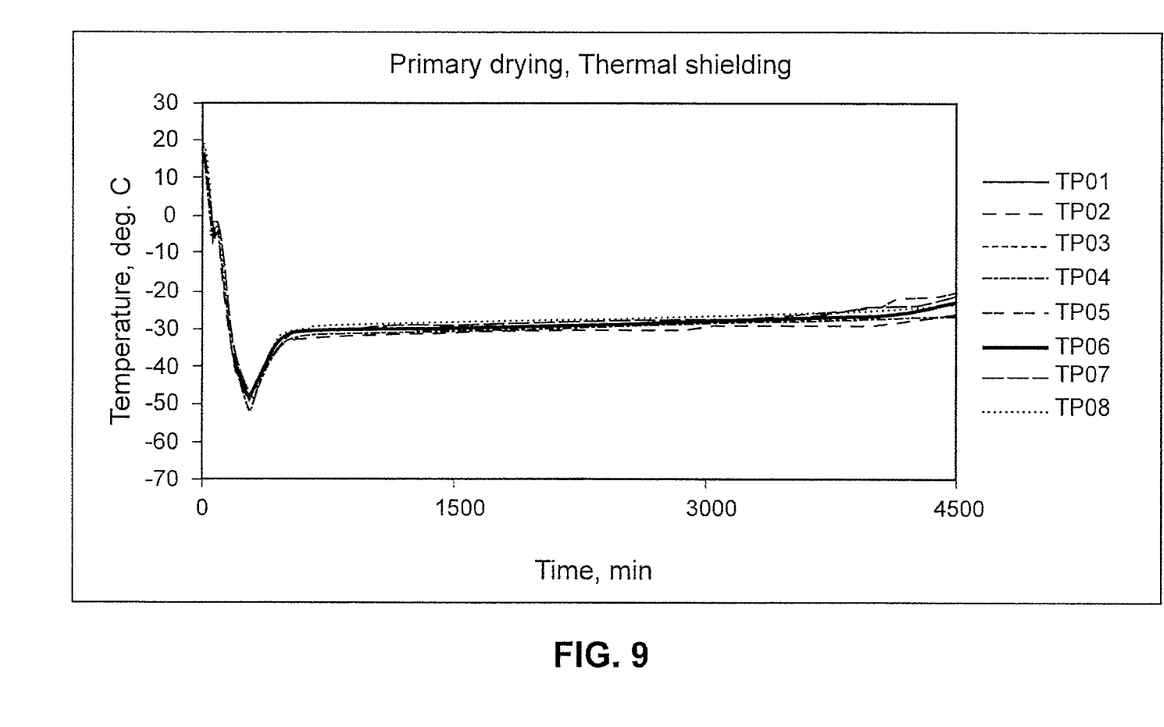
FIG. 9 is a graphical representation of the temperatures sensed by the plurality of temperature probes of FIG. 5 during a drying step of a test lyophilization process conducted with the use of a thermal shield of the present disclosure.

FIGS. 7 and 9 graphically illustrate the temperatures sensed by the temperature probes T01-T08 during the cooling step and the drying step of a test lyophilization process, respectively, wherein the apparatus 300 of FIG. 5 was equipped with a thermal shield 108. As illustrated, the lines on the graph, each of which is assigned to a particular probe T01-T08, follow the same shape and are tightly grouped, showing uniform temperatures at the various locations monitored. Accordingly, the thermal shields 108 disclosed herein advantageously help maintain a uniform temperature distribution amongst the target material 15 stored in the vessels 14 during the lyophilization process.

In view of the foregoing, it should be appreciated that the various embodiments described herein provide examples of various devices, systems, and methods constructed in accordance with the principles of the present disclosure. These embodiments are not meant to be exclusive embodiments, but rather, any of the embodiments can be modified to include any one or more features of any of the other embodiments. As such, it should be appreciated that the examples provided herein are not exhaustive and the various features are interchangeable with each other, as well as with features not specifically disclosed but understood by a person having ordinary skill in the art.

What is claimed:

1. A device for supporting at least one vessel containing a target material to be lyophilized, the device comprising:
    a support panel having a support surface;
    a central region of the support surface for supporting the at least one vessel;
    a perimeter region of the support surface surrounding the central region; and
    a thermal shield positioned on the perimeter region and defining at least one shielding cavity surrounding the central portion to define a storage space on the support surface for accommodating the at least one vessel, the at least one shielding cavity adapted to contain a shielding material during lyophilization that is distinct from the target material.

2. The device of claim 1, wherein the thermal shield comprises:
    an inner wall portion surrounding the central region; and
    an outer wall portion surrounding the inner wall portion and spaced from the inner wall portion to define the at least one shielding cavity.

3. The device of claim 2, wherein the inner and outer wall portions extend perpendicularly from the support surface of the support panel.

4. The device of claim 2, wherein the at least one shielding cavity further comprises a bottom wall portion extending between the inner wall portion and the outer wall portion and disposed directly on the perimeter region of the support surface of the support panel.

5. The device of claim 2, wherein the at least one shielding cavity defined between the inner and outer wall portions of the thermal shield comprises an elongated channel surrounding the central region of the support panel and for containing the shielding material.

6. The device of claim 5, further comprising an elongated opening defined by the elongated channel for enabling at least one component of the shielding material to exhaust from the elongated channel during the lyophilization process.

7. The device of claim 5, further comprising a cap enclosing the elongated channel, the cap defining a plurality of apertures for controlling a rate at which the shielding material exhausts from the channel during the lyophilization process.

8. The device of claim 1, wherein the thermal shield comprises a U-shaped cross-section.

9. The device of claim 1, wherein the thermal shield comprises a plurality of shielding repositories arranged side-by-side on the perimeter region of the support surface and surrounding the central region, wherein each of the plurality of repositories defines a shielding cavity containing the shielding material during the lyophilization process.

10. The device of claim 9, wherein each of the shielding repositories comprises a tube.

11. The device of claim 1, further comprising a shielding material disposed in the at least one shielding cavity.

12. A system for lyophilizing target material stored within at least one vessel, the system comprising:
    a freeze drying machine including a chamber having chamber walls; and
    the device of claim 1 removably supported within the chamber of the freeze-drying machine.

13. A device for supporting at least one vessel containing a target material to be lyophilized, the device comprising:
    a support panel having a support surface;
    an elongated channel disposed on and extending along a perimeter of the support panel and having an inner wall spaced from an outer wall to define a U-shaped cross-section, the elongated channel adapted to contain a shielding material during lyophilization that is distinct from the target material; and
    a storage space positioned on the support surface of the support panel and surrounded by the elongated channel for accommodating the at least one vessel.

14. The device of claim 13, wherein the inner and outer walls extend perpendicularly from the support surface of the support panel.

15. The device of claim 13, further comprising an elongated opening defined by the U-shaped cross-section of the elongated channel and extending along the perimeter of the support panel, the elongated opening for enabling at least one component of the shielding material to exhaust from the elongated channel during the lyophilization process.

16. The device of claim 15, further comprising a cap on the elongated channel and covering the elongated opening, the cap defining a plurality of apertures for controlling a rate at which the shielding material exhausts from the channel during the lyophilization process.

17. The device of claim 13, further comprising a shielding material disposed in the elongated channel.

18. The device of claim 13, wherein the elongated channel further comprises a bottom wall extending between the inner wall and the outer wall and disposed directly on the perimeter of the support surface of the support panel.

19. A system for lyophilizing target material stored within at least one vessel, the system comprising:
    a freeze drying machine including a chamber having chamber walls; and
    the device of claim 13 removably supported within the chamber of the freeze-drying machine.

* * * * *